(12) United States Patent
Bateman

(10) Patent No.: US 6,391,654 B1
(45) Date of Patent: May 21, 2002

(54) SEPARATION AND DETECTION OF SPERMATOZOA

(75) Inventor: Paul North Bateman, Kingston-Upon-Thames (GB)

(73) Assignee: Genosis Limited, Kingston-Upon-Thames (GB)

(*) Notice: Subject to any disclaimer, the term of this patent is extended or adjusted under 35 U.S.C. 154(b) by 0 days.

(21) Appl. No.: 09/658,302

(22) Filed: Sep. 8, 2000

Related U.S. Application Data

(63) Continuation of application No. PCT/GB99/02685, filed on Aug. 13, 1999.

(30) Foreign Application Priority Data

Aug. 14, 1998 (GB) ................................................ 9817795

(51) Int. Cl.$^7$ ..................... G01N 33/543; G01N 33/53; G01N 33/00; B01D 33/00; A01N 1/02

(52) U.S. Cl. ..................... 436/518; 436/536; 436/541; 436/63; 436/164; 436/169; 436/177; 436/178; 436/824; 435/2; 435/7.1; 435/7.9; 435/174; 435/287.1; 435/287.9; 435/288.5; 435/288.6; 435/288.7; 435/814; 422/68.1; 422/101; 422/120; 422/255; 422/261; 210/321.6; 210/348; 210/645; 210/650; 210/651; 210/500.21; 210/767

(58) Field of Search ..................... 422/68.1, 82, 82.05, 422/82.07, 82.08, 101, 120, 255, 261, 267, 939, 947, 948, 56–61; 210/634, 635, 643, 644, 645, 649, 650, 651, 652, 653, 767, 800, 321.6, 508, 511, 513, 348, 500.1, 500.21; 435/2, 7.1, 7.9, 7.92, 176, 177, 287.1–287.32, 187.6–287.7, 288.5, 808, 814, 7.94, 287.8, 287.9, 805; 436/518, 524–532, 541, 547, 63, 164, 168, 169, 172, 177, 178, 800, 805, 815, 824, 808, 810, 536

(56) References Cited

U.S. PATENT DOCUMENTS 3,991,743 A * 11/1976 Bucalo ..................... 128/1 R (List continued on next page.)

FOREIGN PATENT DOCUMENTS

| EP | 0 387 873 A1 | 9/1990 | |
| EP | 0446509 | 9/1991 | .......... A61K/35/52 |
| FR | 2614899 | 11/1988 | ............ C12M/3/00 |
| FR | 2 614 899 | 11/1988 | |
| GB | 2 220 003 A | * 12/1989 | |
| JP | 04200473 | 7/1992 | ............ A61M/1/00 |
| WO | 95/29188 | 11/1995 | |
| WO | WO-96/13225 A2 | * 5/1996 | |
| WO | 97/40386 | 10/1997 | |
| WO | WO-99/66331 A1 | * 12/1999 | |

OTHER PUBLICATIONS

Sanchez et al., A new method for evaluation of the acrosome reaction in viable human spermatozoa. Androlgia. (1991) vol. 23, pp. 197–203.*

(List continued on next page.)

*Primary Examiner*—Long V. Le
*Assistant Examiner*—Kartic Padmanabhan
(74) *Attorney, Agent, or Firm*—Jenkens & Gilchrist, P.C.

(57) ABSTRACT

A kit for testing male fertility comprises a vessel, a base unit, a liquid supply containing liquid and two filters. The first filter is a sample separation filter which forms a hindrance to transmission of spermatozoa. The second filter of the kit is a spermatozoa detection filter comprising a reagent for identifying spermatozoa. Activation of the kit is prevented until a transport medium, such as the liquid, fills a gap allowing spermatozoa to transmit to a detection zone. The kit may be of one-piece construction and utilizes a thin piece of filter material to separate motile from non-motile spermatozoa.

37 Claims, 2 Drawing Sheets

U.S. PATENT DOCUMENTS

| | | | | |
|---|---|---|---|---|
| 4,007,087 A | * | 2/1977 | Ericsson | 195/1.8 |
| 4,804,537 A | * | 2/1989 | Bergman et al. | 424/105 |
| 5,185,246 A | * | 2/1993 | Deutsch | 435/7.21 |
| 5,427,946 A | * | 6/1995 | Kricka et al. | 435/291 |
| 5,575,914 A | | 11/1996 | Jeyendran | 210/445 |
| 5,866,354 A | | 2/1999 | Froman | 435/29 |
| 5,908,380 A | | 6/1999 | Zavos et al. | 600/33 |
| 5,935,800 A | | 8/1999 | Alvarez | 435/7.8 |
| 5,976,389 A | * | 11/1999 | Zavos | 210/807 |
| 6,129,214 A | * | 10/2000 | Bar-Ami et al. | 209/235 |
| 6,153,104 A | * | 11/2000 | Robertson | 210/650 |
| 6,153,373 A | * | 11/2000 | Benjamin et al. | 435/2 |
| 6,171,778 B1 | * | 1/2001 | Ellington et al. | 435/2 |

OTHER PUBLICATIONS

Agarwal et al. Filtration of spermatozoa through L4 membrane: a new method. Fertility and Sterility. (1991) vol. 56, No. 6, pp. 1162–1165.*

Copy of International Search Report dated Jan. 14, 2000 for PCT/GB99/02685.

* cited by examiner

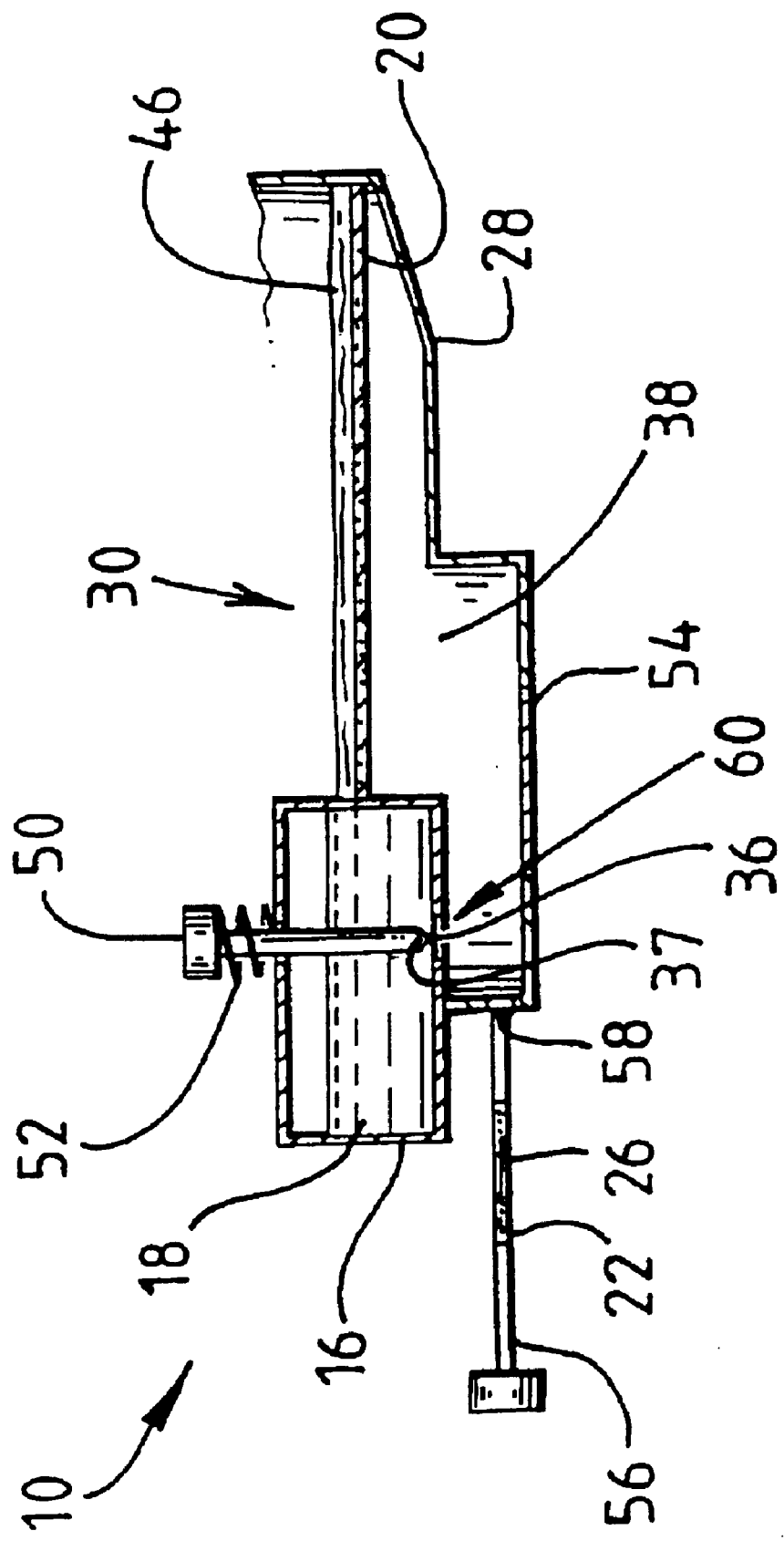

SEPARATION AND DETECTION OF SPERMATOZOA

This application is a continuation of International Application No. PCT/GB99/02685, filed on Aug. 13, 1999, pending, which claims the benefit of British Patent Application No. 9817795.9 filed on Aug. 14, 1998.

TECHNICAL FIELD

This invention relates to the separation and detection of spermatozoa. It provides methods and kits for the separation and/or detection of motile spermatozoa in a sample, which are useful in a number of applications, including the diagnosis and treatment of male infertility.

BACKGROUND ART

It has been estimated that approximately 14–16% of all couples attempting to conceive experience difficulty, and are defined by fertility therapists as infertile. 40% of these cases result from male factors. In a substantial proportion of these, treatment is available to ameliorate or relieve the condition which leads to infertility.

Other conditions also exist in which it is desirable to test for the presence or otherwise of viable spermatozoa in a sample. For example, vasectomies are now frequently carried out as a method of contraception, but it is necessary to verify the effectiveness of a vasectomy by confirming that ejaculate is free of viable spermatozoa for a period of time after the operation.

A number of methods exist for assessing the motility and number of spermatozoa in a sample. One such method is microscopic analysis, which is typically carried out in a hospital or commercial laboratory. More recently, however, a number of proposals have been made for test kits which are intended to simplify the detection of spermatozoa, and which may therefore be useful in the diagnosis of male infertility. For example, WO97/40386 discloses a kit which is based on the detection of the 34 kD human epididymal spermatozoa protein (P34H). This protein is thought to be involved in spermatozoa-zona pellucida interaction. The test kit disclosed in WO97/40386 uses an antibody raised against P34H or a related antigen, and a reagent for detecting antibody binding to P34H. As disclosed in WO97/40386, spermatozoa in a test sample are washed three times by centrifugation in Dulbecco-phosphate buffered saline. The samples are then heat denatured at 95° C., centrifuged at 14000 g, and the supernatants are then used for analysis.

EP-A-0387873 also discloses a kit for the evaluation of male fertility. This kit uses solid beads to which is bound an antibody specific to an antigenic site on the human spermatozoon acrosome. Such beads are mixed with a test sample, and incubated for a period of 10 to 30 minutes. The test beads are then separated from the suspension, washed and subjected to measurement of the number of spermatozoa bound to the solid beads, preferably by examination with the aid of a microscope.

A kit for the detection of spermatozoa in a sample is also disclosed in WO95/29188. In this case, the test is based on antibodies to an antigen such as the SP-10 antigen of human spermatozoa.

A significant disadvantage of the test kits disclosed in the prior art mentioned above is that they do not distinguish between motile and non-motile spermatozoa. In the detection of male infertility, the ability to assess the numbers of motile spermatozoa is the most predictive indicator of male infertility. Moreover, many of the prior art test kits involve procedures, such as centrifugation or microscopic examination, which do not lend themselves to home use, instead requiring implementation by a skilled practitioner.

It is therefore desired to provide a device, which can be self contained or provided in a plurality of components, and a method for separating motile spermatozoa from non-motile spermatozoa, and for collecting and detecting the presence of the motile spermatozoa.

DISCLOSURE OF INVENTION

The invention provides an apparatus for separating motile spermatozoa from non-motile spermatozoa in a liquid sample, the apparatus comprising (i) a vessel having a sample receiving inlet, a filtered sample outlet and a sample separation filter mounted therebetween, the sample separation filter having a sample-receiving surface and an opposed surface, and the sample separation filter being effective substantially to prevent flow of the sample therethrough, but permitting passage of motile spermatozoa therethrough when said opposed surface of said sample separation filter is placed in contact with a liquid medium and (ii) means for supplying a liquid to said opposed surface of said filter. The sample may comprise motile spermatozoa, non-motile spermatozoa and/or spermatozoa with reduced motility.

In order to detect the separated motile spermatozoa, spermatozoa detection means such as a spermatozoa detection filter may be provided at a sample outlet side of the sample separation filter, and spaced therefrom. The detection means may be integral with the apparatus, or it may be provided as a separate component thereof for inserting into the apparatus before, during or after placing the filter in contact with the liquid medium. The spermatozoa detection filter may have similar characteristics to the sample separation filter.

The filters may have a thickness of 100–2000 μm, preferably 200–1000 μm, and more preferably 400–800 μm. For example, the filters may have a thickness of about 600 μm. The minimum particle retention size of the filters may be 5–100 μm, preferably 8–60 μm, and more preferably 10–40 μm. The filters may be fibrous, for example made of glass wool or polypropylene, or they may have a gel or a foam construction. For gel or foam constructions that are not self supporting, an underlying grid lattice or other support may be provided. A particularly preferred filter is a glass fibre filter, which may include a binder such as an acrylic ester. It will be appreciated that the use of a gel as the filter can avoid the need to supply liquid to its opposed surface, because the gel itself acts as suitable means for achieving this. Preferred gels are hyaluronic acid and methylcellulose.

A reagent or a combination of reagents may be located in the spermatozoa detection means which are directly or indirectly capable of generating a visual signal on interaction with spermatozoa. These reagent or combination of reagents may include antibodies that detect an antigen present on spermatozoa and/or may be capable of binding spermatozoa. Spermatozoa, when immobilised by such antibodies, could be visually detected using a visually detectable reagent which binds to spermatozoa. Antibodies to CD59, as discussed in WO99/66331, the complete disclosure of which are incorporated herein by reference, have been found to be suitable for this purpose.

A spermatozoa chemoattractant, such as follicular fluid as identified in WO99/66331, may be located in the spermatozoa detection means. Such spermatozoa chemoattractants are preferably located in a portion of the spermatozoa detection means distal from the sample separation filter.

A pick-up zone may be located either in the sample separation filter or the spermatozoa detection means, said pick-up zone comprising a reagent or combination of reagents which is/are capable of binding to spermatozoa and being transported therewith through the filter(s) to a detection area of the spermatozoa detection means. The reagent or combination of reagents of the pick-up zone may include antibodies that detect an antigen present on spermatozoa. These antibodies may be detectably labelled, for example with gold particles.

The antibodies that are located in the detection area of the spermatozoa detection means may recognise the same or a different spermatozoa antigen from those located in the pick-up zone.

The spermatozoa detection means may comprise a spermatozoa acrosome-lysing reagent and a means for detecting pH change. The spermatozoa acrosome-lysing reagent is typically a lysis buffer, and may comprise Proteinase K or the calcium ionophore A24297. The means for detecting pH change could be a pH sensitive probe or a pH indicator reagent capable of visually detecting a pH change, for example bromocresol purple.

The sample receiving surface of the sample separating filter may contain an enzymatic liquefaction agent, such as chymotrypsin, capable of causing semen liquefaction. The invention also provides a male fertility testing kit comprising an apparatus as described above, the kit further comprising a liquid release mechanism, wherein upon activation of the liquid release mechanism, liquid from a liquid supply is applied to said opposed surface of the sample separation filter to provide liquid communication with a spermatozoa detection means.

The spermatozoa detection means may be integral with the apparatus or it may be provided as a separate or separable component of the kit.

The kit may comprise an integral liquid supply, or an external liquid supply may be used. It will be appreciated that the liquid must be one in which motile spermatozoa remain motile for a sufficient period of time to migrate to the spermatozoa detection means, ie. the liquid is generally non-toxic to spermatozoa. However, the liquid may be such that is has a toxicity to spermatozoa that is sufficiently low that enough spermatozoa will successfully reach the detecting means. The liquid is preferably a buffer such as phosphate buffered saline (PBS) or Earle's Balanced Salt Solution (EBSS), as described in WO99/66331.

It will be appreciated that, where a gel-based filter is used, the gel can act as its own liquid supply. It may be desirable, however, to supply liquid to the opposed surface of a gel-based filter, for instance to dilute a sample after separation through the filter.

The kit may comprise two or more separable components, for example the apparatus and a base unit for the apparatus to engage with. Application of the apparatus to the base unit may be adapted to activate the liquid release mechanism, thereby wetting the spermatozoa detection filter and sample separation means. Alternatively, a button release for the liquid may be provided. The wetting of the spermatozoa detecting filter may activate the detecting agents applied to the spermatozoa detecting means.

An overflow container for catching excess liquid applied to the apparatus upon activation of the liquid release mechanism may be provided.

The liquid supply may comprise a frangible compartment or portion, wherein the liquid release mechanism breaks the compartment to release liquid contained therein. The liquid thereby released may then be channelled by a ramp towards a well formed between the apparatus and a base portion of the kit. The compartment may be piercable by a liquid release mechanism in the form of a piercing mechanism, for example retained by a stop, the stop preventing the piercing mechanism from piercing the compartment until activated by a user.

The invention also provides a method of detecting the presence of motile sperm in a sample, comprising the steps of providing a filter having first and second surfaces, the filter permitting migration of the motile sperm therethrough when a liquid is applied to the second surface, applying the sample to the first surface, applying a liquid to the second surface, and detecting sperm that has migrated through the filter. The sample may be a mixture comprising motile and non-motile spermatozoa. The filter may be the filter contained within the apparatus or the kit as described above.

BRIEF DESCRIPTION OF DRAWINGS

FIG. 3 shows an alternative embodiment in which the detection means is a separable component of the kit.

MODES FOR CARRYING OUT THE INVENTION

Figure 1:
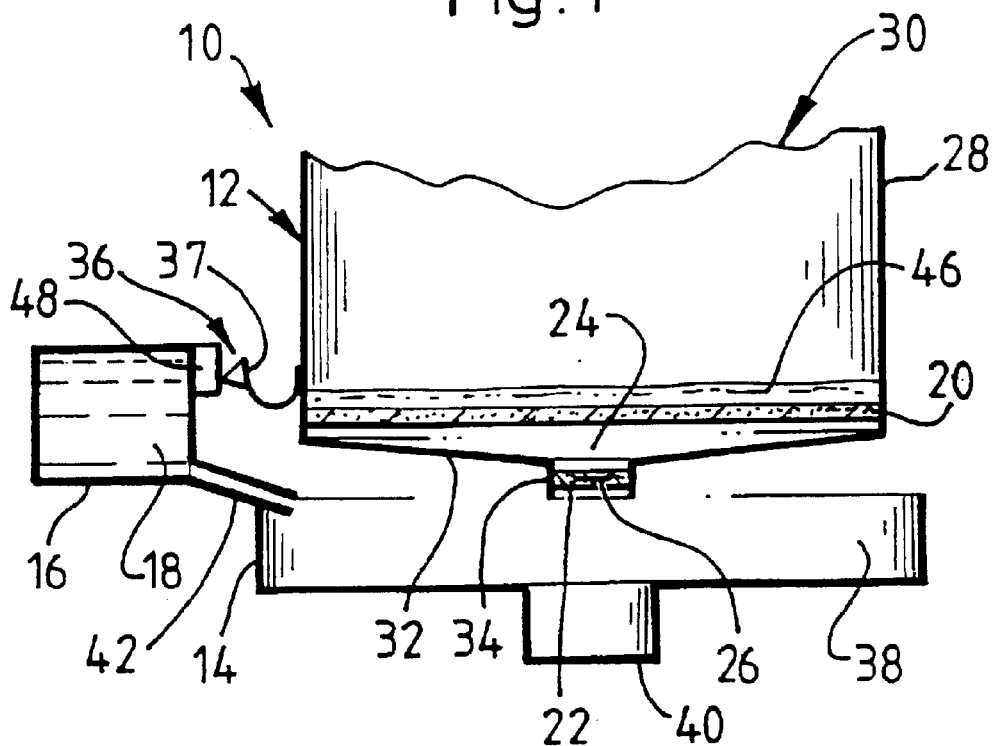
FIG. 1 shows a kit in accordance with the present invention prior to application of a vessel to a base unit.
Figure 2:
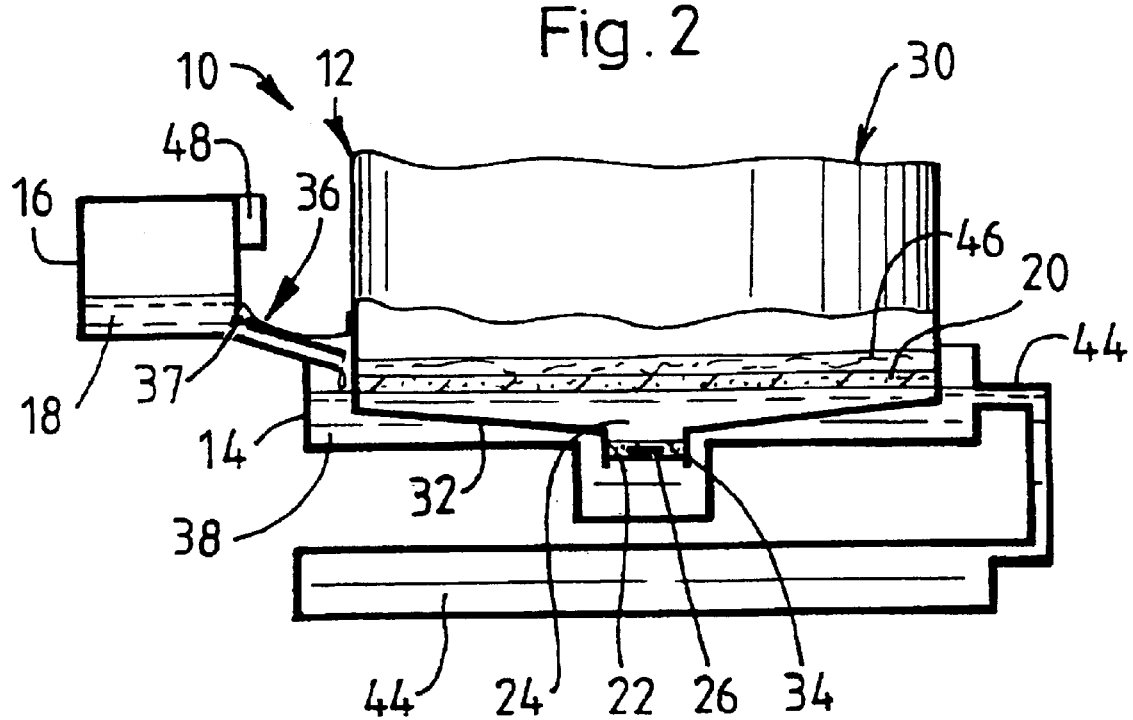
FIG. 2 shows the kit of FIG. 1, with an overflow, after application of the vessel to the base unit.

A kit 10 for testing male fertility is shown in FIGS. 1 and 2. The kit comprises a vessel 12, a base unit 14, a liquid supply 16 containing liquid 18, and two filters 20,22.

The first filter 20 is a sample separation filter 20 which forms a hindrance to transmission of spermatozoa due to the composition and construction thereof. For example, the filter will substantially retain on a sample receiving surface thereof seminal fluid and non-motile spermatozoa present in a sample deposited thereon. This may be by virtue of the pore size of the filter, for example. Non-motile spermatozoa will not pass through the filter. However, where the spermatozoa are motile, they will be able to "swim" through the filter.

The head of a human spermatozoon is typically 3–5 $\mu$m in diameter, and tail length is approximately 50–60 $\mu$m. The filter should be such that these spermatozoa can swim through the filter upon application of the liquid to the opposed surface. Suitable filter materials may be identified by a series of simple experiments.

Experiment 1: The assessment of sperm toxicity

A swim up from a semen sample is prepared (Practical Laboratory Andrology—David Mortimer, page 272) and the resultant preparation of motile spermatozoa is used for the assessment of sperm toxicity of the filter. A 2 cm by 2 cm square of the filter is cut into 2 mm by 1 cm strips. 3×1 ml aliquots of the freshly prepared motile sample are added to round bottom tubes (eg., Falcon no. 2001 or 2037) marked duplicate A, duplicate B and control C. 10 of the thin strips of filter are placed in each of duplicate A and B. A, B and C are then incubated at 37° C. for 1 hour with frequent agitation. Sperm motility and/or sperm vitality assessment is then performed (Practical Laboratory Andrology, pages 49–50 for motility and pages 66–69 for vitality) on both duplicates and the control. A marked difference in sperm motility and or vitality between the filter containing sample and the control indicates that the filter is toxic to sperm.

Experiment 2: The evaluation of sperm "wicking" through a filter

200 µl of liquefied semen is placed in a round bottom tube. A 0.5 cm by 4 cm strip of filter is then introduced to the semen sample, such that only the lower 1–2 mm of the filter is in direct contact with the semen sample. In some filters, the semen sample will move by capillary action or "wick" up the filter taking with it motile and non-motile spermatozoa, therein invalidating the separation. The extent of wicking in a given time frame eg. 15 minutes, can be determined by removing the filter from the semen sample and analysing with light microscopy 2 mm segments of the filter for the presence of spermatozoa. In order to be an effective separator of motile spermatozoa from a mixture of motile and non-motile sperm, the extent of wicking in the filter (in the time frame that the sample will be left applied to the filter prior to detection or collection of the filtered motile sperm) should be less than the thickness of the filter.

Experiment 3: Efficacy of a filter to prevent the passage of dead or immobile spermatozoa A sample of dead or immobilised sperm is obtained by either heating a semen sample at 95° C. in a water bath or by adding a 10% cyanide solution. 200 µl of a dead or immobilised semen sample is applied to the upper surface of the filter, the underside of the filter being in direct communication with 1 ml of EBSS. After 5, 10, 15 and 30-minute intervals, a 10 µl aliquot of the filtrate is removed and examined under light microscopy for the presence of spermatozoa. An effective filter will not allow the passage of dead or immobile spermatozoa for the duration that the semen sample is required to be in contact with the upper surface of the filter.

Experiment 4: Efficacy of a filter to selectively allow the passage of motile spermatozoa An assessment of the wet preparation of a semen sample is performed (Practical Laboratory Andrology, pages 49–50) and the characteristics noted. 250 µl of the semen sample is applied to the upper surface of the filter, the underside of the filter being in direct communication with 1 ml of EBSS. After 5, 10, 15 and 30-minute intervals, a 10 µl aliquot of the filtrate is removed and examined under light microscopy for the presence of motile spermatozoa and the ratio of motile versus non-motile spermatozoa in the filtrate compared to that of the original sample. An effective filter should allow the passage of motile spermatozoa. For example if the original semen sample had a motility of 40% (ie. 60% of spermatozoa are non-motile), the filtrate should preferably have a motility of at least 90% with less than 10% being non-motile.

The second filter 22 of the kit is a spermatozoa detection filter 22. The spermatozoa detection filter 22 forms a detection zone 26 for the spermatozoa that can migrate through the sample separation filter 20. The detection zone 26 is provided within the spermatozoa detection filter 22, and comprises a reagent capable of generating a signal upon interaction with spermatozoa. However, a gap 24 is formed between the two filters 20,22 to prevent activation of the kit until such time that a transport medium, for example the liquid 18 in the liquid supply 16, has been supplied to fill the gap 24 to enable the spermatozoa to be transmitted to the detection zone 26, and thus the fertility test to be conducted with the kit.

The composition and construction of suitable filters 20,22 and the detection zone 26 may be such as that described herein, or such as that described in further detail in the prior art. However, preferable compositions and constructions are as described in WO99/66331, the complete disclosures of which are incorporated herein by reference. A particularly preferred filter material is identified as Filter 4622, available from Ahlstrom Filtration, Inc., 122 W. Butler Street, PO Box A, Mt. Holly Springs, Pa. 17065–0238, U.S.A. It comprises a micro glass fibre with an acrylic binder. The acrylic latex is an anionic dispersion of acrylate polymers and copolymers in a water base. These polymers are based on acrylic esters. The pore size is 20 µm and the thickness is 580 µm.

The vessel 12 has a circular cross section with a side wall 28, an open top 30, an annular base 32 and an open nozzle 34 formed on the annular base 32. The spermatozoa detection filter 22 is provided within the nozzle 34. A cap (not shown) may be placed onto the open top 30 for maintaining a sterile environment within the vessel 12. The cap over the open top 30 would need to be removed for application of a sample into the vessel 12.

The base unit 14 comprises the liquid supply 16, a liquid release mechanism 36 and a well 38. The well 38 comprises a hole 40 adapted to receive the nozzle 34. The hole 40 may have a window (not shown) provided therein for inspection of the detection zone 26 after activation of the kit 10. The base unit 14 further comprises a ramp 42 for channelling liquid 18 from the liquid supply 16 into the well 38, and an overflow 44 for catching excess liquid 18 provided into the well 38 from the liquid supply 16.

The liquid release mechanism 36 is in the form of a piercing member 37 adapted to be activated by application of the vessel 12 onto the base unit 14. Prior to activation of the piercing member 37, the piercing member 37 is retained by a stop 48. Application of the vessel 12 draws the piercing member 37 past the stop 48. A frangible portion may be provided for the liquid supply 16 for puncturing with the piercing member 37 as it draws past the stop 48. This frangible portion may comprise a tin-foil wall section.

Experiment 5: Separation of motile spermatozoa using gel filters

Various gel-like filters can be used for the spermatozoa separation. The gel media were obtained from Sigma-Aldrich or Pharmacia-Upjohn and were resuspended in EBSS (Gibco-BRL). Four different hyaluronic acid gels and one methylcellulose gel were tested.

Flattened glass capillary tubes (Camlab), with dimensions 1.2×4.8 mm and an inner diameter vision path of 0.4 mm, were filled with the resuspended media, with one end sealed. The open end of the tube was placed in a 1.5 ml microfuge tube containing 100 µl or 200 µl liquefied semen. Sperm were allowed to migrate into the gel for 30 min at room temperature, and the tube was wiped and observed under the microscope.

The numbers of spermatozoa at 1 cm distances from the open end of the tube were recorded in order to assess the penetration and migration in the various gels. Numbers of spermatozoa per field of view, using ×10 or ×20 objectives and a ×10 eyepiece to give final magnification of ×100 or ×200, were counted on an Olympus BH-2 microscope. The area observed at 100× magnification was 0.785 mm$^2$; at 200× magnification, the area was 0.196 mm$^2$.

The results for the four hyaluronic acid products were as follows:

| Gel concentration (mg/ml) | Initial number of sperm (× 10⁶) | Initial sperm motility (%) | Magnifⁿ | Number of spermatozoa |  |  |  |
|---|---|---|---|---|---|---|---|
| | | | | 1 cm | 2 cm | 3 cm | 4 cm |
| Hyaluronic acid 1 — MW: 3–5.8 × 10⁶, from human umbilical cord ||||||||
| 1 | 91 | 69 | × 20 | 180 | 50 | 30 | — |
| 0.5 | | | | 150 | 38 | 20 | — |
| Hyaluronic acid 2 — MW: ~2 × 10⁶, from rooster comb ||||||||
| 5 | 126 | 79 | × 20 | 69 | 12 | 5 | — |
| 2 | | | | — | — | — | — |
| 1 | | | | 300 | 2 | — | — |
| 0.5 | | | | 150 | 2 | — | — |
| Hyaluronic acid 3 — MW: 0.85–1.6 × 10⁶, from *Streptococcus zooepidemicus* ||||||||
| 2 | 126 | 79 | × 20 | 40 | 7 | 4 | — |
| 1 | | | | 59 | 1 | — | — |
| 0.5 | | | | 16 | 2 | — | — |
| Hyaluronic acid 1 — Healonid from Pharmacia-Upjohn ||||||||
| 1.25 | 95 | 69 | × 20 | 300 | 180 | 22 | 5 |
| 0.625 | | | | 280 | 130 | 15 | 5 |

The results for methylcellulose at a viscosity of 15 cp were as follows:

| Gel concentration (mg/ml) | Initial number of sperm (× 10⁶) | Initial sperm motility (%) | Magnifⁿ | Number of spermatozoa |  |  |  |
|---|---|---|---|---|---|---|---|
| | | | | 1 cm | 2 cm | 3 cm | 4 cm |
| Semen sample 1 ||||||||
| 10 | 22 | 79 | × 20 | 68 | 4 | — | — |
| 0.55 | | | | 74 | 4 | 1 | — |
| 2 | | | | 80 | 8 | — | — |
| 1 | | | | 50 | 4 | — | — |
| 0.5 | | | | 23 | 6 | — | — |
| Semen sample 2 ||||||||
| 20 | 52 | 61 | × 10 | 10 | — | — | — |
| 10 | | | | 116 | 20 | 5 | — |
| 5 | | | | 115 | 8 | 3 | — |
| 2.5 | | | × 20 | 82 | 12 | 3 | — |
| Semen sample 3 ||||||||
| 10 | 33 | 88 | × 10 | 80 | 1 | — | — |
| 5 | | | | 68 | — | — | — |
| Semen sample 4 ||||||||
| 10 | 91 | 69 | × 20 | 120 | 6 | 2 | — |

The results for meethylcellusose at viscosity of 4000 cp were as follows

| Gel concentration (mg/ml) | Initial number of sperm (× 10⁶) | Initial sperm motility (%) | Magnifⁿ | Number of spermatozoa |  |  |  |
|---|---|---|---|---|---|---|---|
| | | | | 1 cm | 2 cm | 3 cm | 4 cm |
| Semen sample 1 ||||||||
| 10 | 160 | 80 | × 20 | 250 | 62 | 18 | — |
| 5 | | | | 150 | 5 | — | — |
| Semen sample 2 ||||||||
| 10 | 5 | 64 | × 10 | 5* | — | — | — |
| 5 | | | | 1* | — | — | — |
| Semen sample 3 ||||||||
| 10 | 160 | 0 | × 10 | — | — | — | — |
| 5 | | | | — | — | — | — |
| Semen sample 4 ||||||||
| 10 | 66 | 75 | × 10 | 120 | 8 | — | — |
| 5 | | | | 80 | 2 | — | — |
| Semen sample 5 ||||||||
| 10 | 33 | 88 | × 10 | 510 | 8 | — | — |
| Semen sample 6 ||||||||
| 10 | 101 | 64 | × 20 | 250 | 50 | 28 | 12 |

*these two measurements taken at 0.25 cm from open end

It is evident, therefore, that gels can be used as filters to separate motile sperm from a sample spermatozoa.

A process of performing a male fertility test with the above-described kit will now be described.

A sample of seminal fluid 46, or ejaculate, is deposited within an unused or recycled vessel 12 through the open top 30 and onto the sample separation filter 20. The sample may be deposited, for example, by direct application by the user, or by a pipette application from an ejaculated semen sample, The thereby primed vessel 12 is then applied to an unused or recycled base unit 14 which has a fresh liquid supply 16 such that the nozzle 34 of the vessel 12 is inserted within the hole 40 of the base unit 14. During the application of the vessel 12 to the base unit 14, the side wall 28 of the vessel 12 activates the piercing member 37 to puncture the liquid supply 16, as shown in FIG. 2, in which the piercing member 37 has pierced through the frangible portion of the liquid supply 16. Alternatively, a piercing button 50, see FIG. 3, may be provided for piercing the liquid supply 16.

Upon piercing the liquid supply 16, the liquid 18 contained within the liquid supply 16 is channelled down the ramp 42 into the well 38, filling the hole 40 and the well 38 with liquid 18, the liquid 18 also entering through the nozzle 34 of the vessel 12, which is located within the hole 40 of the base unit 14. Thereby, the liquid passes through the spermatozoa detecting filter 22 to fill the gap 24 between the two filters 20,22 with the liquid 18. Excess liquid 18 overflows the well 38 and is collected by the overflow 44.

The liquid 18 acts as a transport medium for spermatozoa that has migrated through the sample separation filter 20 to permit the spermatozoa to migrate beyond the sample separation filter 20 towards the spermatozoa detecting filter 22, so that it may be detected by the detection zone 26 within the spermatozoa detecting filter 22. Upon detection of spermatozoa at the detection zone 26, a signal is produced by the reagent provided thereat, thus signifying presence of motile spermatozoa. In the absence of motile spermatozoa in the sample, no spermatozoa will reach the detection zone 26 since non-motile or reduced-motile spermatozoa will not pass through the sample separation filter 20.

The kit 10 of FIG. 3 is an alternative embodiment of the present invention. It has an open top 30 exposing a sample separation filter 20 as described above. A sample 46 is shown deposited onto the sample separation filter 20 on a sample receiving surface thereof.

The side wall 28 of the kit 10 defines a well 38. A liquid supply 16 is provided integral with the kit 10, adjacent the well 38, the liquid supply 16 containing liquid 18 and having a frangible portion 60 on a periphery thereof for separating the liquid supply 18 from the well 38 prior to activation of the kit 10. A spermatozoa detection filter 22 is provided on a slide member 56 which may be slidably attached to the kit 10, or it may be provided as a separate component of the kit insertable through a sealable opening 58 in the side wall 28 for conducting a detection of spermatozoa within the well 38.

The liquid release mechanism comprises a piercing button 50 and a piercing member 37. The piercing button 50 is biased into a non-piercing position by a spring 52. Pressing the piercing button drives the piercing member 37 through the frangible portion 60 of the liquid supply, thus allowing liquid 18 contained in the liquid supply 16 to flow into the well 38.

Alternatively, the slide member 56 could be adapted to release the liquid 18 within the liquid supply 16 automatically upon insertion thereof within the well 38, for example by providing a piercing member thereon which would pierce the frangible portion 60 of the liquid supply 16.

A transparent window 54 is provided in the side wall 28 of the well 38 to enable an inspection of the detecting zone 26 contained within the spermatozoa detecting filter to be performed. However, the side wall 28 may be manufactured of a transparent material, thus avoiding the need for the window 54.

The principle of use for the kit 10 of FIG. 3 is similar to that of the embodiments of FIGS. 1 and 2. However, the liquid 18 may be released into the well prior, during or after insertion of the spermatozoa detecting filter within the well.

It will, of course, be understood that the present invention, and in particular the kit and a method of its use, has been described above purely by way of example. Modifications may be made whilst remaining within the scope and spirit of the invention.

What is claimed is:

1. An apparatus for separating motile spermatozoa from non-motile spermatozoa in a liquid sample, the apparatus comprising (i) a vessel having a sample receiving inlet, a filtered sample outlet and a sample separation filter mounted therebetween, the sample separation filter having a sample-receiving surface and an opposed surface, and the sample separation filter being effective to prevent flow of the sample therethrough, but permitting passage of motile spermatozoa therethrough when only said opposed surface of said sample separation filter maintains contact with a non-sample liquid medium and (ii) means for supplying a non-sample liquid to only said opposed surface of said filter, and further comprising a spermatozoa detection means on an outlet side of the sample separation filter, and spaced therefrom, and a liquid release mechanism, wherein upon activation of the liquid release mechanism, liquid from an integral liquid supply is applied to the sample filtered end of the sample separation filter to provide liquid communication with the spermatozoa detection means.

2. An apparatus according to claim 1, wherein the sample separation filter is of a gel or foam construction.

3. An apparatus according to claim 1, wherein the filter is fibrous.

4. An apparatus according to claim 3, wherein the fibrous filter is made of glass wool or polypropylene.

5. An apparatus according to claim 1, wherein the sample additionally comprises spermatozoa with reduced motility.

6. An apparatus according to claim 2, wherein the sample additionally comprises spermatozoa with reduced motility.

7. An apparatus according to claim 3, wherein the sample additionally comprises spermatozoa with reduced motility.

8. An apparatus according to claim 4, wherein the sample additionally comprises spermatozoa with reduced motility.

9. An apparatus according to claim 1, wherein the detection means is integral with the apparatus.

10. An apparatus according to claim 1, wherein the detection means is a separable component of the apparatus for inserting into the apparatus before, during or after placing the sample separation filter in contact with the liquid medium.

11. An apparatus according to claim 1, wherein the filter has a thickness of 100–2000 $\mu$m.

12. An apparatus according to claim 11, wherein the filter has a thickness of 200–1000 $\mu$m.

13. An apparatus according to claim 11, wherein the filter has a thickness of approximately 400–800 $\mu$m.

14. An apparatus according to claim 12, wherein the filter has a thickness of about 600 uM.

15. An apparatus according to claim 1, wherein the filter has a minimum particle retention size of 5–10 $\mu$m.

16. An apparatus according to claim 15, wherein the filter has a minimum particle retention size of approximately 8–60 $\mu$m.

17. An apparatus according to claim 15, wherein the filter has a minimum particle retention size of approximately 10–40 $\mu$m.

18. An apparatus according to claim 2, wherein the filter has an underlying grid lattice for supporting the filter.

19. An apparatus according to claim 1, wherein a reagent or a combination of reagents directly or indirectly generates a visual signal on interaction with spermatozoa located in the spermatozoa detection means.

20. An apparatus according to claim 19, wherein the reagent or combination of reagents include antibodies that detect an antigen present on spermatozoa and bind spermatozoa.

21. An apparatus according to claim 20, wherein spermatozoa, when immobilized by the antibodies, are visually detectable using a visually detectable reagent which binds to spermatozoa.

22. An apparatus according to claim 1, wherein a spermatozoa chemoattractant is located in the spermatozoa detection means.

23. An apparatus according to claim 22, wherein the spermatozoa chemoattractant is located in a portion of the spermatozoa detection means distal from the sample separation filter.

24. An apparatus according to claim 1, wherein a pick-up zone is located either in the sample separation filter or the spermatozoa detection means, said pick-up zone comprising a reagent or combination of reagents which binds spermatozoa and are transported therewith to a detection area of the spermatozoa detection means.

25. An apparatus according to claim 24, wherein the reagent or combination of reagents of the pick-up zone include antibodies that detect an antigen present on spermatozoa.

26. An apparatus according to claim 25, wherein the antibodies that detect an antigen present on spermatozoa are detectably labeled.

27. An apparatus according to claim 26, wherein the antibodies that detect an antigent present on spermatozoa are detectably labeled with gold particles.

28. An apparatus according to claim 25, wherein the antibodies that are located in a detection area of the spermatozoa detection means recognize a different spermatozoa antigen compared to the antibodies located in the pick-up zone.

29. An apparatus according to claim 25, wherein the antibodies that are located in a detection area of the spermatozoa detection means recognize the same spermatozoa antigen as the antibodies located in the pick-up zone.

30. An apparatus according to claim 1, wherein the spermatozoa detection means comprises a spermatozoa acrosome-lysing reagent and a means for detecting pH change.

31. An apparatus according to claim 30, wherein the spermatozoa acrosome-lysing reagent is a lysis buffer.

32. An apparatus according to claim 31, wherein the lysis buffer comprises Proteinase K or calcium ionophore A24297.

33. An apparatus according to claim 30, wherein the means for detecting pH change is a pH sensitive probe.

34. An apparatus according to claim 30, wherein the means for detecting pH change is a pH indicator reagent.

35. An apparatus according to claim 34, wherein the pH indicator reagent is bromocresol purple.

36. An apparatus according to claim 1, wherein the sample receiving surface of the sample separating filter contains an enzymatic liquefaction agent.

37. A method of detecting the presence of motile sperm in a sample,
   (a) providing the apparatus of any one of claims 1 to 36,
   (b) applying the sample to a first surface of the sample separation filter,
   (c) applying a non-sample liquid to the opposing surface of the sample separation filter,
   (d) providing a well for containing said non-sample liquid, and
   (e) detecting sperm that has migrated through the filter and through said liquid non-sample.

* * * * *